(12) United States Patent
Long et al.

(10) Patent No.: US 7,973,210 B2
(45) Date of Patent: Jul. 5, 2011

(54) METHODS FOR ASSISTING CAREGIVERS IN FACILITATING TOILET TRAINING

(75) Inventors: Andrew Mark Long, Appleton, WI (US); Richard D. Mosbacher, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 377 days.

(21) Appl. No.: 12/164,811

(22) Filed: Jun. 30, 2008

(65) Prior Publication Data

US 2009/0326491 A1    Dec. 31, 2009

(51) Int. Cl.
*A61F 13/15* (2006.01)
(52) U.S. Cl. .................. 604/361; 604/359; 604/385.01
(58) Field of Classification Search .......... 604/361, 604/359, 385.01
See application file for complete search history.

(56) References Cited

U.S. PATENT DOCUMENTS

| | | | |
|---|---|---|---|
| 4,940,464 A | 7/1990 | Van Gompel et al. | |
| 5,058,088 A | 10/1991 | Haas et al. | |
| 5,602,804 A | 2/1997 | Haas | |
| 5,681,298 A | 10/1997 | Brunner et al. | |
| 5,719,828 A | 2/1998 | Haas et al. | |
| 5,766,389 A | 6/1998 | Brandon et al. | |
| 5,785,354 A | 7/1998 | Haas | |
| 6,200,250 B1 | 3/2001 | Janszen | |
| 6,250,929 B1 | 6/2001 | Kolb et al. | |
| 6,295,252 B1 * | 9/2001 | Holt et al. | 368/327 |
| 6,417,455 B1 | 7/2002 | Zein et al. | |
| 6,642,427 B2 * | 11/2003 | Roe et al. | 604/361 |
| 6,645,190 B1 | 11/2003 | Olson et al. | |
| 6,752,430 B2 | 6/2004 | Holt et al. | |
| 2004/0055367 A1 | 3/2004 | Swiecicki et al. | |
| 2005/0137543 A1* | 6/2005 | Underhill et al. | 604/361 |
| 2006/0114754 A1 | 6/2006 | MacDonald et al. | |
| 2007/0149936 A1 | 6/2007 | Weber et al. | |

FOREIGN PATENT DOCUMENTS

| | | |
|---|---|---|
| JP | 2002022688 | 1/2002 |
| JP | 2004529730 | 9/2004 |
| WO | WO 00/37009 | 6/2000 |

OTHER PUBLICATIONS

International Search Report, PCT/IB2009/052040, filed May 15, 2009.

* cited by examiner

*Primary Examiner* — Jacqueline F. Stephens
(74) *Attorney, Agent, or Firm* — Dority & Manning, P.A.

(57) ABSTRACT

A method for assisting a caregiver in determining when to select a next generation product for facilitating toilet training. The method includes the steps of providing information to a caregiver about a second absorbent product, such as a next generation product, while the caregiver is using a first absorbent product in conjunction with a child. The child, for instance, may not have started toilet training or may be in the process of toilet training. Based upon a behavioral or wetness characteristic of the child, recommendations are made to the caregiver when it is time to switch to the next generation product to facilitate toilet training. For instance, in one embodiment, the method may include comparing a wetness characteristic of the child with a readiness target. Once the readiness target is met, a recommendation may be made to the caregiver to switch to a product that includes a toilet training feature not present in the product currently being worn by the child.

20 Claims, 2 Drawing Sheets

METHODS FOR ASSISTING CAREGIVERS IN FACILITATING TOILET TRAINING

BACKGROUND

Little boys and girls normally wear diapers until they are ready for the toilet training process, when they learn to use the toilet by themselves. The point at which a child will begin this training process is dependent upon many factors, some of which are psychological, some physiological, and some unique to the individual child or their environment.

The toilet training process has been studied and found to encompass multiple stages, ranging from early stages of training characterized by behaviors such as understanding potty words to late stages of training characterized by behaviors such as using a regular toilet without a potty seat. As part of the toilet training process, the parent or caregiver desirably provides instruction and positive encouragement and/or reinforcement that the child should now be using a toilet, instead of diapers. The use of training pants is desirable at some point in the process because it represents a change from diapers to a product form that mimics underwear in the way it is donned, closer to the way that grownups dress and use the toilet.

The toilet training process is complicated by the fact that the successes that a child achieves at any particular stage may also depend upon many factors. These too can be psychological, physiological, or related to the individual child or their environment. Unfortunately, if the child does not respond to an initial toilet training instruction or introduction, the parent or caregiver can be at a loss for identifying more suitable products, training aids or techniques. This tendency is increased by the difficulty in assessing the amount of physiological readiness and or progress a child is making, specifically how long a child is staying dry and how large their voids are (indicators of progress or readiness) is masked by the high capacity of absorbent products.

One or more proposed methods for improving the effectiveness of a child's toilet training regime are disclosed in U.S. Pat. No. 6,250,929, which is incorporated herein by reference. The '929 patent is directed to a method that utilizes a progress scale to evaluate the child's current level or stage of toilet training. The method also provides feedback in the form of specific toilet training recommendations that are matched to the child's current stage of toilet training. The '929 patent represents great advances in the art.

The present disclosure is directed to further improvements in methods for assisting caregivers, such as parents, in toilet training children. For example, many caregivers do not recognize when a child is ready to be toilet trained and also have difficulties in determining when to transition from one absorbent product (e.g. diapers) to another absorbent product (e.g. absorbent pants) may help facilitate faster and/or easier toilet training. The present disclosure is directed to a method for assisting caregivers in choosing and selecting an absorbent product based upon the wetness characteristics of the child. More particularly, the present disclosure is directed to a method for assisting caregivers in switching from a first product to a next generation product during the child's development. The present disclosure is also directed to a method for providing feedback to a caregiver regarding the progress that is being made in toilet training a child.

SUMMARY

In general, the present disclosure is directed to a method for assisting a caregiver in determining when to select a next generation product for facilitating toilet training. The present disclosure is also directed to a method for indicating to a caregiver the amount of progress that is occurring during toilet training. In one embodiment, for instance, the method can include the steps of using a first absorbent product on a child that is not toilet trained. The first absorbent product can include indicia regarding at least one readiness target. The readiness target, for instance, may comprise a behavioral characteristic of the child that, once met, may indicate its time for the child to further advance in toilet training. For instance, the readiness target can be related to a wetness characteristic of the child.

While the child is using the first absorbent product, the method of the present disclosure can further include the step of providing information to a caregiver about a second absorbent product. The second absorbent product, for instance, may possess a toilet training feature not present in the first absorbent product. The information about the second absorbent product can be communicated to the caregiver in various ways. For instance, in one embodiment, the information about the second absorbent product may appear directly on the first absorbent product or on the packaging in which the first absorbent product is contained. For example, the information about the second absorbent product may comprise printed matter appearing on the first absorbent product or the packaging.

In an alternative embodiment, the information regarding the second absorbent product is conveyed to a caregiver through a component that may be used in conjunction with the first absorbent product. For example, the first absorbent product may contain a wetness sensing system that includes a signaling device. The signaling device may comprise an electronic device that is used in conjunction with the first absorbent product. The signaling device may be used to relay information to the caregiver about alternative product choices that will help facilitate training.

In accordance with the present disclosure, the method further includes the step of recommending to the caregiver to switch from the first absorbent product to the second absorbent product when the at least one readiness target has been reached by the child. The recommendation to switch to the second absorbent product may be communicated to the caregiver in any of the ways described above.

In one embodiment, the first absorbent product may contain an indicator that monitors one or more wetness characteristics of the child that is or are related to the readiness target. The wetness characteristic may comprise, for instance, the length of time the child can maintain a dry state in the first absorbent product and/or the amount of urine the child discharges into the first absorbent product in a single voiding when wetting the product. The indicator contained in the first absorbent product may comprise a wetness sensing system as described above or any other suitable device, such as a void volume indicator that is intended to qualitatively or quantitatively measure the amount of urine the child discharges into the first absorbent product. The indicator contained in the first absorbent product can then be used by the caregiver to compare the wetness characteristic of the child with the readiness target in order to assess the child's progress towards toilet training.

Once toilet training has begun, the present disclosure is also directed to different methods for providing feedback to the caregiver regarding the progress the child is making. For instance, during toilet training, the wetness characteristic may be continually monitored as a means to assess the child's progress. For example, increases in void volume over time, increases in the time between voids (i.e. urine discharges) and/or increases in the frequency of the child attempting to use a proper toilet may provide feedback to the caregiver that toilet training progress is occurring and that the process choices and/or product choices the caregiver has made are becoming effective.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
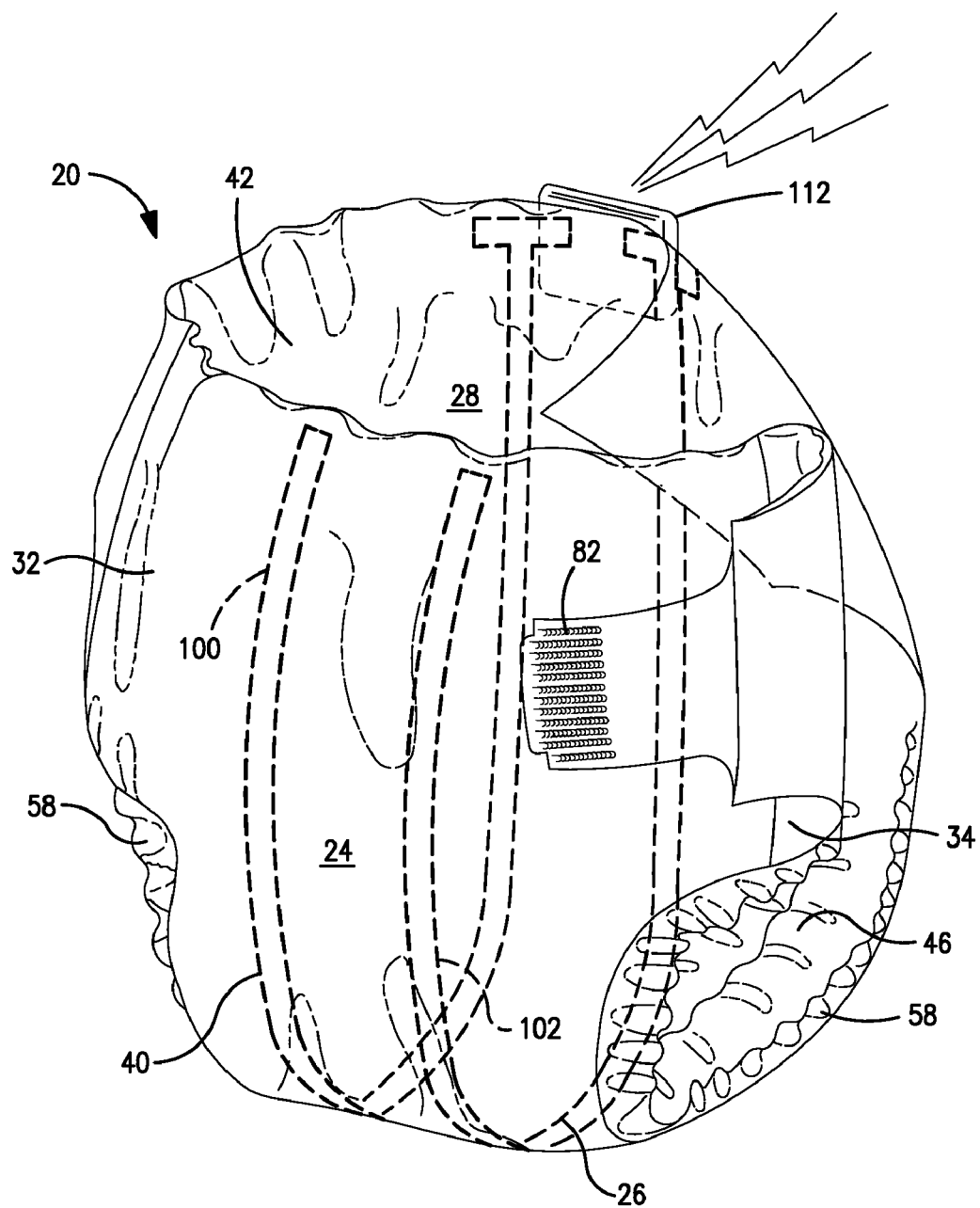
FIG. 1 is a perspective view of one embodiment of an absorbent product that may be used in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

Caregivers, including parents, often have a difficult time recognizing when a child is ready for toilet training and if a child is making progress during toilet training. In addition, if problems arise during toilet training, caregivers can also fail to recognize or appreciate different strategies that may be available to assist in the process. For example, various absorbent products are commercially available that can assist a caregiver in initiating a toilet training regime and/or can assist a caregiver when problems arise during toilet training.

In general, the present disclosure is directed to a method for assisting caregivers, including parents, in selecting the correct absorbent product for use with the child during the toilet training process. More particularly, the method includes providing information to a caregiver about other absorbent products during use of a first absorbent product. The other absorbent products, for instance, may comprise next generation products that include one or more features intended to assist caregivers in toilet training children. In one embodiment, for instance, the information about the next generation products can appear directly on the absorbent product currently being used or on the packaging in which the absorbent product is contained.

According to the present disclosure, one or more indices can be associated with the absorbent product being used that provide recommendations or advice to the caregiver regarding the appropriate time to switch from the product currently being used to a different absorbent product. The switch to the second absorbent product, for instance, can be recommended in order to initiate toilet training or to otherwise help advance the toilet training process. For example, a different product may be recommended when toilet training progress slows or is stymied with a particular child in a given product form.

In one embodiment, the recommendation or suggestion to switch to a next generation product may be based upon one or more behavioral characteristic or wetness characteristic of the child.

For example, various wetness characteristics of the child can be used to determine whether a child is ready for a toilet training regime and whether a child is making progress once toilet training has begun. For example, signs that show the child has developed bladder control are particularly relevant to whether the child is ready for toilet training. Bladder control, for instance, is evidenced by longer periods of time in between wetting a diaper, greater amounts of urinal discharge and the like. The child's desire to use the toilet or ability to use a toilet are also highly indicative signals that the child may be ready to advance to different generation absorbent products that may assist the child in becoming completely toilet trained.

In one embodiment, the absorbent product currently being used by the child may include one or more indicators that monitor or otherwise provide information regarding at least one wetness characteristic of the child during use. In accordance with the present disclosure, the product may indicate to the caregiver a readiness target that relates to the one or more wetness characteristics. Once the child is capable of achieving the readiness target, for instance, the absorbent product or an associated component may then communicate to the caregiver that it is time to switch to the next generation product. The readiness target, for instance, can be a length of time the absorbent product remains dry, may be related to the amount of urine discharged into the product, or may relate to some other various characteristic of the child. The product form could be simple pull-on products, pull on products with a visual indicator of wetness to the child, or pull on products with sensation elements to give tactile feedback to the child that they have wet, or pull on products with a auditory alarm to cue the child and caregivers that they are going (or have gone).

Various different absorbent products may be used in accordance with the methods of the present disclosure. In one embodiment, for instance, the method of the present disclosure may utilize an absorbent product that contains a wetness detection system as illustrated in FIG. 1. Referring to FIG. 1, an absorbent product 20, such as a diaper is shown. The absorbent product 20 can comprise any suitable absorbent product without limitation. In the embodiment illustrated, for instance, the absorbent product 20 includes a chassis 32 that, in this embodiment, encompasses a front region 22, a back region 24, and a crotch region 26. The chassis 32 can be made from various materials. In one embodiment, for instance, the chassis 32 includes an outer cover 40 and a bodyside liner 42 that may be joined to the outer cover 40 in a superimposed relation. The liner 42, for instance, may be suitably joined to the outer cover 40 along the perimeter of the chassis 32 to form a front waist seam and a back waist seam. In addition, the liner 42 may be suitably joined to the outer cover 40 to form a pair of side seams in the front region 22 and the back region 24. The liner 42 is positioned relative to the other components in the product so as to be disposed towards the wearer's skin during wear of the product.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded carded webs or foams.

The bodyside liner 42, on the other hand, may be suitably compliant, soft feeling and non-irritating to the wearer's skin. The bodyside liner 42 is also sufficiently liquid permeable to permit liquid body exudates to readily penetrate through its thickness. A suitable bodyside liner 42 may be manufactured from a wide selection of web materials, such as porous foams, reticulated foams, apertured plastic films, woven and nonwoven webs, or a combination of any such materials. In one embodiment, the bodyside liner 42 may comprise a meltblown web, a spunbond web, or a bonded carded web. The bodyside liner 42 may be composed of substantially hydrophobic material and the hydrophobic material may optionally be treated with a surfactant.

The chassis 32 can further include an absorbent structure disposed between the outer cover 40 and the bodyside liner 42 for absorbing liquid body exudates exuded by the wearer. The absorbent structure can be any structure or combination of components which are generally compressible, conformable, non-irritating to a wearer's skin, and capable of absorbing and retaining liquids and certain body wastes. For example, the absorbent structure may include an absorbent web material of cellulosic fibers, other natural fibers, synthetic fibers, woven or nonwoven sheets, scrim netting, or other stabilizing structures, superabsorbent material, binder materials, surfactants, selected hydrophobic materials, pigments, lotions, odor control agents or the like, as well as combinations thereof. In one embodiment, the absorbent structure is a matrix of cellulosic fluff and superabsorbent hydrogel-forming particles.

As is known in the art, the chassis can also include a pair of containment flaps 46 secured to the bodyside liner 42 for inhibiting the lateral flow of body exudates. The containment flaps 46, which may be elasticized, define a partially unattached edge which assumes an upright configuration in at least the crotch region 26 of the absorbent product 20 to form a seal against the wearer's body. The containment flaps 46 can extend longitudinally along the entire length of the chassis 32 or may extend only partially along the length of the chassis.

To further enhance containment and/or absorption of body exudates, the absorbent product 20 may also suitably include leg elastic members 58. The leg elastic members 58 can be operatively joined to the outer cover 40 and/or the bodyside liner 42 and positioned in the crotch region 26 of the absorbent product 20.

The leg elastic members 58 can be formed of any suitable elastic material. Suitable elastic materials include, for instance, sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

As shown in FIG. 1, the absorbent product 20 may further include a pair of opposing elastic side panels or tabs 34. The elastic side panels 34 may be stretched around the waist and/or hips of a wearer in order to secure the garment in place. In the embodiment shown, the elastic side panels are attached to the back region of the chassis. In an alternative embodiment, however, the elastic side panels may be attached to the front region of the chassis.

In an alternative embodiment, most or all of the chassis can be made from elastic materials. In this embodiment, for instance, the side panels 34 may be integral with the chassis 32.

In order to hold the absorbent product in place on a wearer, the product may include a fastening system that, once secured, defines a 3-dimensional product having a waist opening opposite a pair of leg openings. In the embodiment illustrated, the fastening system includes a hook and loop fastener. For instance, as shown in FIG. 1, the elastic side panel 34 is connected to a hook material 82 which is intended to wrap around the product and engage the outer surface of the product where a suitable loop material may exist.

In addition to hook and loop fasteners, however, it should be understood that any suitable fastening system may be incorporated into the product. For example, in an alternative embodiment, a pressure sensitive adhesive may be used to fasten the side panels around the wearer. Other suitable fasteners include cohesive fasteners, mechanical fasteners, and the like. Other suitable mechanical fasteners may include buckles, snaps, etc.

For use in accordance with the methods of the present disclosure, the absorbent product 20 further includes a wetness sensing system. The wetness sensing system includes a first conductive element 100 spaced from a second conductive element 102. In this embodiment, the conductive elements extend from the front region 22 of the wetness sensing absorbent article to the back region 24 without intersecting. The conductive elements 100 and 102 can comprise any suitable conductive material, such as a conductive thread or a conductive foil for example include 112-S silver metallic conductive paste (ink) from Electroscience Laboratories, Inc. and conductive foil described in U.S. Pat. No. 6,417,455 issued Jul. 9, 2002 to Zein et. Al. The first conductive element 100 may not intersect the second conductive element 102 in order to form an open circuit that may be closed, for instance, when a conductive fluid is positioned in between the conductive elements. In other embodiments, however, the first conductive element 100 and the second conductive element 102 may be connected to a sensor within the chassis. The sensor may be used to sense changes in temperature, may be used to sense the presence of a particular substance, such as a metabolite or may sense fluid volume in addition to fluid presence.

The conductive elements 100 and 102 may be incorporated into the chassis 32 at any suitable location as long as the conductive elements are positioned so as to contact a body fluid that is absorbed by the absorbent product. In this regard, the conductive elements 100 and 102 generally lie inside the outer cover 40. In fact, in one embodiment, the conductive elements 100 and 102 may be attached or laminated to the inside surface of the outer cover 40 that faces the absorbent structure 44. Alternatively, however, the conductive elements 100 and 102 may be positioned on the absorbent structure 44 or positioned on the liner 42.

The conductive element 100 and 102 may be connected directly to a signaling device 112, either through direct or indirect contact. The first conductive element 100 may be attached to a first conductive pad member 104, while the second conductive element 102 may be connected to a second conductive pad member 106. The pad members 104 and 106 may be provided for making a reliable connection between the open circuit formed by the conductive elements to the signaling device 112 that is intended to be installed on the chassis by the consumer or manufacturer.

In accordance with the present disclosure, the signaling device 112 may be configured to monitor or sense at least one wetness characteristic of the wearer. Based upon the wetness characteristic in relation to a readiness target, a recommendation or suggestion can be made to the caregiver to either continue using the same absorbent product or to switch to a different absorbent product. Monitoring the wetness characteristic can also provide feedback to the caregiver as to the progress a child is making to completely become toilet trained.

The manner in which this information is communicated to the consumer or the caregiver can vary dramatically depending upon the particular application. In one embodiment, for instance, the signaling device 112 can be configured to communicate all of this information to the caregiver. For instance, the signaling device may monitor a wetness characteristic and compare the wetness characteristic to a readiness target. Once the readiness target has been met, the signaling device can then indicate to the caregiver that the child is ready for a different product that may facilitate the toilet training process. The recommendation or suggestion to switch to a different product, for instance, can, in one embodiment, simply be an audible or visible signal present on the signaling device. For example, the signaling device may include one or more lights that change color (i.e. from red to green) which then indicates to the consumer that a product change is now recommended. Alternatively the choice of auditory cue could change in conjunction with the chosen sign of readiness.

In an alternative and perhaps more sophisticated process, the signaling device may be configured to communicate with an electronic communication medium such as an interactive web-site accessible via the internet. The signaling device can be connected to the web-site, for instance, in order to download any information stored in the signaling device. Based on the information and data received, the web-site can produce a recommendation or suggestion to switch to a different product or to remain with the same product. In this embodiment, the web-site may be configured to use the data and to select a particular product from a series of multiple and different products that would be best suited for the child based upon the child's particular wetness characteristics. The product selection, for instance, may be based not only on one or more wetness characteristics but also on various input that may be added to the web-site by the user. Such other information may include various physical traits of the child, such as sex, height, weight, and age.

In still another embodiment, the suggestion or recommendation to switch to a new product may be communicated to the caregiver through printed matter appearing directly on the product currently being used by the child or on the packaging in which the product is contained. For instance, in this embodiment, the signaling device 112 may be used to monitor or sense one or more wetness characteristics of the child. The caregiver may then compare the wetness characteristics obtained from the signaling device to one or more readiness targets that may be communicated to the caregiver through printed matter. Once the readiness target has been met, the printed matter can then communicate to the caregiver a recommendation to switch products in order to facilitate toilet training.

The switch from the first absorbent product to the second absorbent product can vary depending upon the development of the child. In one embodiment, for instance, the recommendation may be to switch from a diaper to a training pant, such as to initiate toilet training. The use of training pants is desirable at some point in the toilet training process because it represents a change from diapers to the way that grownups dress and use the toilet.

In an alternative embodiment, the first product and the second product may both comprise diapers or training pants but the second product may contain or possess a toilet training feature not present in the first product. For instance, should difficulties arise during toilet training, the recommendation or suggestion may be to switch to a product that provides further reinforcement or may possess a training aid that can assist the child in toilet training by either encouraging the child to use the toilet and/or by discouraging a child from wetting the absorbent product.

For example, in one embodiment, the recommendation may be to switch from a first training pant product to a second training pant product. In this embodiment, the second training pant product may include a feature not on the first product, such as graphics that encourage a child to use the toilet. In one embodiment, for instance, the graphics may comprise a cartoon that disappears if the product is wetted thus discouraging a child from wetting the product.

In another embodiment, the second absorbent product may contain a cooling device that, when wetted, provides the wearer with a cooling sensation. The cooling sensation may discourage the child from wetting the product or at least provide a signal to the child that the product has been wetted and that the child should consider using a toilet. The use of a product containing a cooling device as described above, for instance, may be well suited to instances where the child is wetting the product at night and the cooling device is used to wake the child up during the incident.

In general, any suitable cooling device may be incorporated into the product. In one embodiment, for instance, the cooling device may include a temperature change composition that, when wetted, changes temperature to provide the cooling sensation. Examples of temperature change compositions that may be used are disclosed in U.S. Pat. No. 5,681,298 and in U.S. Patent Application Publication No. 2007/0149936, which are both incorporated herein by reference.

Figure 2:
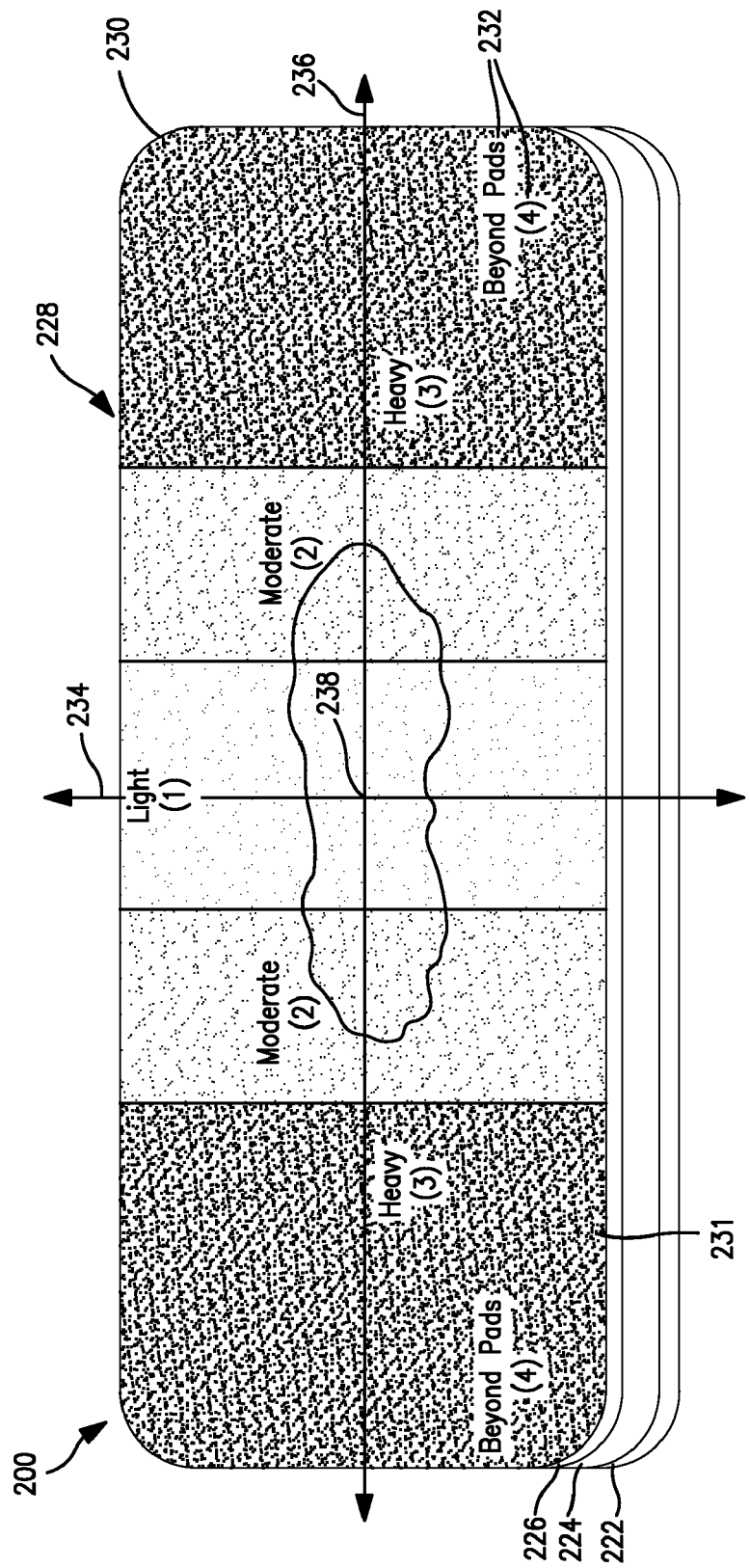
FIG. 2 is a plan view of one embodiment of a void volume indicator that may be used in accordance with the present disclosure.

In the embodiment illustrated in FIG. 1, a signaling device 112 is used to monitor at least one wetness characteristic. It should be understood, however, that numerous other constructions are available for monitoring wetness characteristics. For example, in one embodiment, the wetness characteristic may be monitored or sensed by another type of indicator. For instance, as shown in FIG. 2, in one embodiment, the first absorbent product may include a void volume indicator generally 200. Void volume indicators can be provided in order to either directly or indirectly indicate the amount of urine that is discharged into the absorbent article. Greater amounts of urine that are discharged into the absorbent article during wetting indicate a child's ability to control his or her bladder and thus be ready for a toilet training regime. Examples of void volume indicators that may be incorporated into products in accordance with the present disclosure are disclosed in U.S. Patent Application Publication No. 2004/0055367, which is incorporated herein by reference.

As shown in FIG. 2, the void volume indicator 200 includes a plurality of wetness indication zones which can each have a primary wetness indicator and where the plurality of indication wetness zones provide feedback to indicate progressively increasing void volumes and thus urine volume. In one embodiment, for instance, each zone may change to a different color as the urine spreads through the absorbent structure.

More particularly, the void volume indicator 200 includes a plurality of wetness indication zones 228. The wetness indication zones can have any suitable shape which correspond to increasing void volumes that are absorbed by the pad. The concentric zones, for instance, can be circular, can have an oval shape or can a complex shape. In the embodiment illustrated in FIG. 2, the wetness indication zones are rectangular areas 231. The rectangular areas 231 are oriented such that their length is parallel to a transverse central axis 234 and their width is parallel to a longitudinal central axis 236. The void volume indicator 200 works by wicking urine and other fluids progressively farther away from a center 238 where ideally the insult occurs.

The void volume indicator 200 as shown in FIG. 2 is intended to be incorporated into an absorbent product. In this regard, the void volume indicator 200 includes an absorbent structure 224 positioned in between a bottom sheet 222 and a top sheet 226. The top sheet 226 and the bottom sheet 222 may comprise the liner and outer cover of an absorbent product or vice versus.

The number of wetness indication zones 228 provided will depend upon the particular product and the accuracy needed.

In one embodiment, each wetness indication zone 228 can contain a primary wetness indicator 230 and a secondary wetness indicator 232. The primary wetness indicator 230 may comprise a color. The secondary wetness indicator 232, on the other hand, may comprise indicia such as words, numbers, letters or symbols. In an alternative embodiment, however, the void volume indicator may only include a single wetness indicator.

The wetness indicators can, depending upon the particular application, indicate qualitatively the amount of fluid absorbed by the product or can indicate the volume of fluid quantitatively, such as in milliliters, ounces or the like.

In still another embodiment, the void volume indicator 200 can include electronics that may communicate with a signaling device such as the one shown in FIG. 1. The signaling device, for instance, can indicate the spread of fluid and thus indicate to a user the amount of urine or other fluid present in the product after being wetted.

In one particular embodiment, for instance, the signaling device may emit a pulsed input signal into the absorbent article in order to approximate the amount of a void. Even in an un-calibrated state, the signaling device may self-align and compare void volumes, based upon the amount of change in the pulsed signal amplitude. As the data is collected, simple peak maximums may be compared to determine if a readiness target has been met. The simple peak maximums may also be used to provide feedback to the caregiver to determine if progress is being made during toilet training. If progress is being made while toilet training is occurring, for instance, the caregiver may want to remain with the current product. If void volumes are not increasing, however, the caregiver may want to consider changing products.

The void volume indicator 200 as shown in FIG. 2 can also be configured to communicate to a caregiver not only information about the relative volume of fluid absorbed by the product but also can be configured to be used in association with a readiness target that may indicate to the caregiver that it is time to switch products. For example, the readiness target may comprise a particular volume of fluid that, once reached or consistently reached by the child, indicates that the child has the necessary bladder control to initiate toilet training. Thus, the method of this present disclosure provides a direct objective way for a caregiver to determine when it is time for toilet training to begin.

The readiness target and the recommendation to switch products can be communicated to the caregiver in conjunction with the void volume indicator 200 using any of the methods described above in conjunction with the wetness sensing system as shown in FIG. 1.

In still another embodiment, instead of a void volume indicator as shown in FIG. 2, the first absorbent product may contain an indicator that measures the amount of time the product is dry after being donned by the child. The length of time it takes for a child to wet an absorbent product, for instance, also is an indicator of bladder control. Dry time can be measured and sensed using various techniques. For instance, in one embodiment, the wetness sensing system shown in FIG. 1 can include a timer built into the signaling device 112 for determining the dry time.

In an alternative embodiment, various other dry time indicators are available and may be used in conjunction with the present disclosure. For instance, various devices or concepts that communicate the relative passage of time are disclosed in U.S. Pat. No. 5,058,088, U.S. Pat. No. 5,719,828, U.S. Pat. No. 5,785,354, U.S. Pat. No. 5,602,804, and U.S. Pat. No. 6,752,430 which are all incorporated herein by reference and may be used in conjunction with an absorbent product for carrying out the methods of the present disclosure.

One particular dryness indicator well suited for use in an absorbent product is disclosed in U.S. Patent Application Publication No. 2006/0114754, which is also incorporated herein by reference. In general, the device includes an indicator panel or display area on a substrate that is enclosed in an envelope or other packaging. The display device may encompass a variety of surfaces or shapes. For instance, the basic indicator panel may be a flat, essentially two-dimensional surface. Alternatively, the indicator panel may have a three-dimensional curved surface, or be part of a shaped article or geometric form. The envelope is at least partially transparent to permit the user to observe the indicator area. On the indicator panel is situated either a design or some other visual configuration having a number of visually distinct sections or zones arrayed spatially relative to each other. The device further includes at least a self-contained reservoir that is in controlled communication with the indicator panel and the envelope enclosing the indicator panel. The system as a whole can be referred to as a chromatogram, since the indicator panel functions analogous to the absorbent column or strip of material containing the stratographically differentiated constituents separated from a solution of mixture by chromatography.

The reservoir contains an activating agent. The activating agent, once triggered or released from the reservoir interacts with the indicator panel. The activating agent generates a mobile front in or on the indicator panel, which passes along the indicator panel carrying along with it colorant from each of the visually distinct sections. Each of the visually distinct sections may be arrayed either adjacent to one another or spaced apart. Each section may be either monochromatic or multi-chromatic. Desirably, each section is monochromatic and of a different, contrasting color from its neighbor. Each visually distinct section may have colorant initially set up as a line or design pattern with a width that can expand and grow in area, even filling up the section and becoming more visually conspicuous, as the mobile front passes through.

As the mobile front progresses, it triggers the movement of the colorant from each section, which can be carried along either to the boundary of or into an adjacent section. The indicator panel in certain embodiments may be configured to either allow colorant from adjacent sections to bleed into or mix together. Alternatively, so-called "gates" in the indicator panel material can control either the rate or direction of elution of colorant from one section into another. The gates can be designed to stop one colorant or a set of colorants from traveling outside of its own section, hence color development may be confined within each section and not affect neighboring sections, even as the activating agent continues to travel through adjacent sections.

The active portion of the indicator panel can be composed of materials selected from a group of cellulose or cellulose-polymer-based materials (e.g., a strip of wicking material), a gel, a plastic/polymer film, chromatographic separation materials, inorganic particles or oxides (e.g., $SiO_2$, $Al_2O_3$), or combinations of such materials. The reservoir may contain either a liquid or gaseous fluid. The liquid may be either water, a thixotropic material, an alcohol, or non-flammable solvent, or other organic species. For instance, the liquid can be a surfactant, a fatty acid, or an aliphatic alcohol. The gas may be either air, oxygen, carbon dioxide, a reducing gas, an inert gas (e.g., nitrogen, helium, argon), a moist gas (i.e., includes water vapor), or a mixture thereof.

A frangible seal is located between the reservoir and the indicator panel. When the frangible seal is ruptured, the timing element becomes activated, establishing communication between the reservoir contents and the indicator panel. Once activated, the activating agent enters or reacts with the indicator, proceeds along, either on a surface of or within the indicator panel at a predetermined rate. The rate at which the activating agent transgresses the indicator panel is likely to be expressed, for instance, on the order of either minutes, hours, or days, per unit of distance. The device may further include a negative feedback interference agent adapted to disrupt development of the timing element manifested on the face of the indicator panel. The negative feedback interference agent modifies the usual development and appearance of the indicator panel. Preferably, the indicator panel is finely tuned so as to graphically show when the interference occurred. In other words, at the time the negative interference is first introduced to the indicator panel, a mark, such as a chemical signature, or a point or line, will appear on the display, beyond which the activating agent development is either stopped or disrupted.

Thus, in one embodiment, the dryness indicator can be attached to the first absorbent product. When the absorbent product is placed on the child, the frangible seal can be broken to initiate the timing element. Once the product is wetted, the timing element may either stop or indicate the time at which the insult occurs. Through this device, the dryness time of the absorbent article can be measured either qualitatively or quantitatively.

In accordance with the present disclosure, the period of time it takes for the child to wet the absorbent product as may be indicated by the dryness indicator can then be compared to a readiness target that is communicated to the caregiver either directly or indirectly by the absorbent product. When the child has met the readiness target, a recommendation can be made to the caregiver to switch products and assist in toilet training. All of this information can be communicated to the caregiver using any of the methods or techniques described above.

The amount of dry time can be calculated and communicated to the caregiver in different ways. For example, especially when using the signaling device shown in FIG. 1, the amount of dry time can be averaged over days, weeks or months. In one embodiment, the dry time can be segmented according to typical child behavior. For instance, an average dry time may be calculated for different times of the day, such as for instance in the morning, in the afternoon, and in the evening. A separate dry time may be also be calculated while the child is sleeping.

In one embodiment, the dry time can be recorded and stored by communicating with an electronic communication medium, such as an interactive website that may be accessible via the internet. In this manner, dry times can be monitored over a length of time not only to determine whether or not a readiness target is being met, but also to determine whether progress is being made after a caregiver has started toilet training a child. In this manner, the caregiver can be provided feedback that indicates the child's progress. If no progress is being made or if progress is occurring very slowly, a recommendation may be communicated to the caregiver to consider switching to a different product to further facilitate toilet training.

One other wetness characteristic that may be monitored in accordance with the present disclosure is the frequency that a child uses or attempts to use a toilet. In this embodiment, for instance, a proximity detection system may be used in order to monitor the child's behavior. Certain devices or fixtures in the bathroom, for example, may be equipped with proximity detectors to relay audio messages to the child and/or to monitor when the child approaches the device and attempts to use the toilet. The proximity detector, for instance, may not only record the child's use of the toilet but may also relay positive feedback or instructions to the child during toilet training. The feedback or instructions may, for instance, also include actions to be taken for health and hygiene life skills training.

In one embodiment, the proximity detector may wirelessly communicate with a web-based internet site or may wirelessly communicate with the signal device shown in FIG. 1. The signal device can then store the information and directly communicate the information to the caregiver or transfer the information to a web-based internet site.

In still another embodiment, the proximity detector may comprise the signaling device itself. In this embodiment, for instance, a sensor may be placed adjacent to the toilet that wirelessly communicates with the signaling device.

Overall, the proximity detector may send a signal to the caregiver each time the child approaches the toilet as well as track the number of times the child approaches the toilet over time, the duration of time and proximity to the toilet, the time between uses of the toilet, etc. All of this information may be used as an indicator of not only when it may be time to switch products, but may also be used to determine the progress a child is making during toilet training.

It should be understood that more than one wetness characteristic may be monitored in accordance with the present disclosure. For example, proximity detectors as described above may be used in conjunction with void volume indicators, dry time indicators and the like. The information may be used to not only provide recommendations regarding products but can also provide feedback regarding progress a child is making in toilet training and what skills may need more attention. As described above, all of this information may be maintained on a single electronic device, such as the signaling device shown in FIG. 1 or may all be downloaded onto an internet-based website. Communication between the different sensors and the signaling device and/or a web-based site may be wireless or through the use of any suitable interface equipment.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A method for assisting a caregiver in determining when to select a next generation product for facilitating toilet training comprising:

using a first absorbent product on a child that is not toilet trained, the first absorbent product including indicia regarding at least one readiness target, the readiness target being related to a wetness characteristic of the child, the first absorbent product comprising an indicator for sensing the wetness characteristic and wherein the readiness target comprises a length of time the child takes to wet the first absorbent product or comprises an amount of urine the child discharges into the first absorbent product when wetting the product;

providing information to a caregiver about a second absorbent product, the second absorbent product possessing a toilet training feature not present in the first absorbent product; and recommending to the caregiver to switch from the first absorbent product to the second absorbent product when the at least one readiness target has been reached by the child.

2. A method as defined in claim 1, wherein the readiness target comprises the length of time the child takes to wet the first absorbent product.

3. A method as defined in claim 2, wherein the indicator includes a wetness detection system comprising an open circuit that closes when the absorbent product is insulted with urine, the wetness detection system comprising a signal device in communication with the open circuit, and wherein the signal device monitors the length of time the child takes to wet the first absorbent product.

4. A method as defined in claim 3, wherein the signaling device is configured to compare the length of time the child takes to wet the first absorbent product to the readiness target and to generate the recommendation to the caregiver to switch to the second absorbent product once the readiness target has been reached.

5. A method as defined in claim 4, wherein the recommendation delivered to the caregiver by the signaling device comprises an audible signal.

6. A method as defined in claim 4, wherein the recommendation delivered to the caregiver by the signaling device comprises a visual signal.

7. A method as defined in claim 3, wherein the signaling device is configured to be connected to an electronic communication medium for storing data generated by the signaling device and for producing the recommendation.

8. A method as defined in claim 1, wherein the readiness target comprises the amount of urine the child discharges into the first absorbent product when wetting the product.

9. A method as defined in claim 8, wherein the first absorbent product includes a void volume indicator.

10. A method as defined in claim 9, wherein the indicia regarding the at least one readiness target comprises a color change and wherein a certain color change indicates that the readiness target has been met.

11. A method as defined in claim 1, wherein the indicia regarding the readiness target, the information about the second absorbent product, and the recommendation to switch from the first absorbent product to the second absorbent product are communicated to the caregiver directly by the first absorbent product, are communicated to the caregiver by the packaging in which the first absorbent product is contained, or are communicated to the caregiver by a component used in conjunction with the first absorbent product.

12. A method as defined in claim 1, wherein the first absorbent product comprises a diaper and the second absorbent product comprises a training pant.

13. A method as defined in claim 1, wherein the first absorbent product comprises a first training pant and the second absorbent product comprises a second training pant.

14. A method as defined in claim 13, wherein the second training pant contains a cooling device that, when wetted, provides the wearer with a cooling sensation, the cooling device not being present in the first absorbent product.

15. A method as defined in claim 1, wherein the information about the second absorbent product and the recommendation to switch from the first absorbent product to the second absorbent product comprises printed matter appearing on the first absorbent product or on packaging in which the first absorbent product is contained.

16. A method for assisting a caregiver in determining when to select a next generation product for facilitating toilet training comprising:
using a first absorbent product on a child that is not toilet trained, the first absorbent product including indicia regarding at least one readiness target, the readiness target being related to a wetness characteristic of the child, the first absorbent product comprising an indicator for sensing the wetness characteristic;
providing information to a caregiver about a second absorbent product, the second absorbent product possessing a toilet training feature not present in the first absorbent product; and
recommending to the caregiver to switch from the first absorbent product to the second absorbent product when the at least one readiness target has been reached as indicated by the indicator during the sensing of the wetness characteristic.

17. A method as defined in claim 16, wherein the indicator comprises a wetness detection system and wherein the wetness characteristic comprises a length of time the child takes to wet the first absorbent product.

18. A method as defined in claim 16, wherein the indicator comprises a void volume indicator and wherein the wetness characteristic comprises an amount of urine the child discharges into the first absorbent product when wetting the product.

19. A method as defined in claim 16, wherein the information provided to the caregiver about the second absorbent product and the recommendation to the caregiver to switch from the first absorbent product to the second absorbent product are communicated to the caregiver by the first absorbent product or by packaging in which the first absorbent product is contained.

20. A method for assisting a caregiver during toilet training of a child comprising:
monitoring at least one wetness characteristic of the child, the wetness characteristic comprising a void volume of urine discharges, a dry time in between urine discharges, or a frequency of attempts to urinate in a toilet;
comparing recorded information of the wetness characteristic over time to determine if the child is making progress towards toilet training; and
communicating to a caregiver whether progress is occurring; and
further comprising the step of recommending to the caregiver to switch from a first absorbent product to a second absorbent product when the information indicates that progress is not being made.

* * * * *